(12) United States Patent
Cantrell et al.

(10) Patent No.: US 8,623,888 B2
(45) Date of Patent: Jan. 7, 2014

(54) 3-OXY-HYDROMORPHONE DERIVATIVES

(75) Inventors: Gary L. Cantrell, Troy, IL (US); Robert E. Halvachs, Belleville, IL (US); Frank W. Moser, Arnold, MO (US); David W. Berberich, St. Peters, MO (US); Peter X. Wang, Clarkson Valley, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 477 days.

(21) Appl. No.: 12/833,025

(22) Filed: Jul. 9, 2010

(65) Prior Publication Data

US 2011/0015398 A1 Jan. 20, 2011

Related U.S. Application Data

(60) Provisional application No. 61/225,581, filed on Jul. 15, 2009.

(51) Int. Cl.
*C07D 489/02* (2006.01)
*A61K 31/485* (2006.01)

(52) U.S. Cl.
USPC .............................. 514/282; 546/45

(58) Field of Classification Search
USPC ............................. 514/282; 546/45
See application file for complete search history.

(56) References Cited

U.S. PATENT DOCUMENTS

| | | | |
|---|---|---|---|
| 3,299,072 A | 1/1967 | Bartels-Keith | |
| 4,668,685 A | 5/1987 | Shami | |
| 4,673,679 A * | 6/1987 | Aungst et al. | 514/282 |
| 6,365,594 B1 | 4/2002 | Dondio et al. | |
| 7,320,984 B2 * | 1/2008 | Izumimoto et al. | 514/282 |
| 2006/0040970 A1 | 2/2006 | Izumimoto et al. | |
| 2009/0005565 A1 * | 1/2009 | Carroll et al. | 546/46 |
| 2009/0137618 A1 * | 5/2009 | Jenkins | 514/282 |
| 2009/0186832 A1 | 7/2009 | Franklin et al. | |
| 2010/0035826 A1 | 2/2010 | Jenkins et al. | |

FOREIGN PATENT DOCUMENTS

WO WO 2010/045599 4/2010

OTHER PUBLICATIONS

Grinstead, G. A closer look at acetyl and pentafluoropropionyl derivatives for quantitative analysis of morphine and codeine by gas chromatography/mass spectrometry. Journal of Analytical Toxicology. 1991, vol. 15(6), p. 293 (STN Abstract included in submitted prior art).*
Hosztafi, S. et al. Synthesis and analytical characterization of dansyl derivatives of morphine-like substances. Acta Pharmaceutica Hungarica. 1994, vol. 59, p. 22 (STN Abstract included in submitted prior art).*
Grinstead, G. A closer look at acetyl and pentafluoropropionyl derivatives for quantitative analysis of morphine and codeine by gas chromatography/mass spectrometry. Journal of Analytical Toxicology. 1991, vol. 15(6), 293-298.*
Hawley's Condensed Chemical Dictionary (11th Edition., Sax, N. I. and Lewis, R. J. (editors), Van Nostrand Reinhold Co. (NY), 1987, p. 302).*
March's Advanced Organic Chemistry (5th Ed. 2001), 151-155.*
Real World Drug Discovery, Rydzewski (2008), 42-43.*
Database Caplus [Online] Chemical Abstracts Service, Columbus, Ohio, US; 1992, Grinstead: "A closer look at acetyl and pentafluoropropionyl derivatives for quantitative analysis of morphine . . . ", XP 002601489.
Database Caplus [Online] Chemical Abstracts Service, Columbus, Ohio, US; 1985, Yashiki et al.: "Dual mass spectrometry of trifluoroacetyl . . . ", XP 002601490.
Database Caplus [Online] Chemical Abstracts Service, Columbus, Ohio, US; 1967, Bartels-Keith and Hills, "Syntheses related to northebaine. II. Derivatives of . . . ", XP 002601491.
Sagara et al., "Ligand Recognition in μ Opioid Receptor: Experimentally Based Modeling . . . ", Bioorganic & Medicinal Chemistry, 4(12), 1996, pp. 2151-2166, XP 002601492.
Database Caplus [Online] Chemical Abstracts Service, Columbus, Ohio, US; 1994, Hosztafi and Repasi: "Synthesis and analytical characterization of dansyl derivatives of morphine-like substances", XP 002601493.

* cited by examiner

*Primary Examiner* — Joseph Kosack
*Assistant Examiner* — Matthew Coughlin

(57) ABSTRACT

The present invention provides 3-oxy-hydromorphone derivatives, and in particular, 3-ester, 3-carbonate, and 3-sulfonate derivatives of hydromorphone.

15 Claims, No Drawings

3-OXY-HYDROMORPHONE DERIVATIVES

CROSS REFERENCE TO RELATED APPLICATIONS

This application claims the benefit of U.S. Provisional Application No. 61/225,581 filed Jul. 15, 2009, which is incorporated herein in its entirety.

FIELD OF THE INVENTION

The present invention generally relates to 3-oxy-hydromorphone derivatives, and in particular, substituted esters, carbonates, and sulfonates of hydromorphone.

BACKGROUND OF THE INVENTION

Prodrugs are defined as precursors to therapeutic agents that release the active ingredient under the action of metabolic processes. Usually, prodrugs are useful when the active agent has pharmacological insufficiencies, whether on formulation or in delivery. Prodrug activation may occur due to enzymatic and/or non-enzymatic processes in vivo. Prodrug design is particularly applicable when modifying the overall hydrophobic/hydrophilic character of the drug for enhancing absorption into the body.

Hydromorphone is a commonly used analgesic and antitussive agent that is typically delivered orally because the molecule is quite polar. Because of the increasing use of hydromorphone to treat chronic pain, there is a need for transdermal and other delivery systems of this compound. Accordingly, there is a need for hydrophobic derivatives of hydromorphone. Ideally, these hydrophobic derivatives would be in the form of prodrugs that would be converted into active hydromorphone upon transdermal or transmucosal transport.

SUMMARY OF THE INVENTION

Among the various aspects of the present invention is the provision of 3-substituted esters, carbonates, and sulfonates of hydromorphone that have increased hydrophobicity relative to that of unsubstituted hydromorphone.

One aspect of the present invention encompasses a compound comprising Formula (I) or a pharmaceutically acceptable salt thereof:

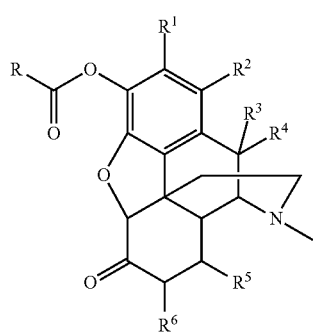

(I)

wherein:

R is selected from the group consisting of hydrocarbyl and substituted hydrocarbyl;

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$ are independently selected from the group consisting of hydrogen, hydrocarbyl, and substituted hydrocarbyl.

Another aspect of the present invention provides a compound comprising Formula (II) or a pharmaceutically acceptable salt thereof:

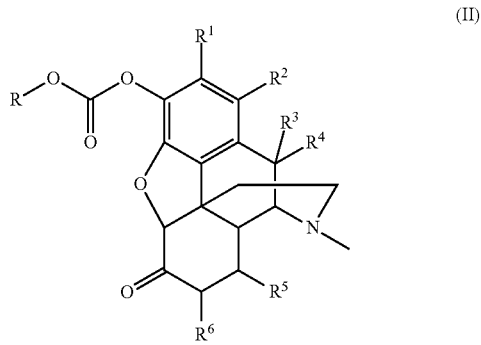

(II)

wherein:

R is selected from the group consisting of hydrocarbyl and substituted hydrocarbyl;

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$ are independently selected from the group consisting of hydrogen, hydrocarbyl, and substituted hydrocarbyl.

A further aspect of the invention encompasses a compound comprising Formula (III) or a pharmaceutically acceptable salt thereof:

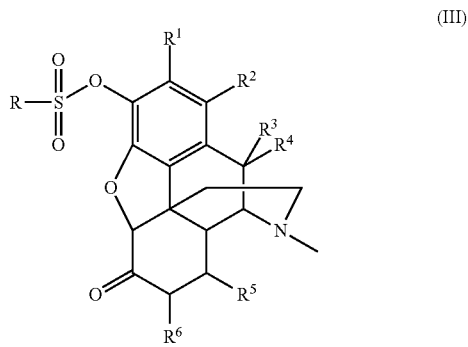

(III)

wherein:

R is selected from the group consisting of hydrocarbyl and substituted hydrocarbyl;

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$ are independently selected from the group consisting of hydrogen, hydrocarbyl, and substituted hydrocarbyl.

Other aspects and features of the invention are detailed below.

DETAILED DESCRIPTION OF THE INVENTION

The present invention provides 3-oxy-hydromorphone derivatives. The compounds of the invention may function as prodrugs, such that they are converted to hydromorphone in vivo. Furthermore, the compounds of the invention have increased hydrophobicity such that they may be administered topically, i.e., transdermally or transmucosally.

(I) Compounds of the Invention

The compounds of the invention are morphinan compounds. For the purposes of discussion, the ring atoms of a morphinan compound are numbered as diagrammed below. Morphinan compounds have asymmetric centers. In particular, the core morphinan compound may have four chiral carbons; namely, C-5, C-13, C-14, and C-9.

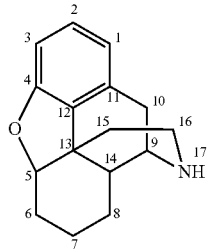

(a) 3-Substituted Esters of Hydromorphone

One aspect of the present invention encompasses a compound comprising Formula (I) or a pharmaceutically acceptable salt thereof:

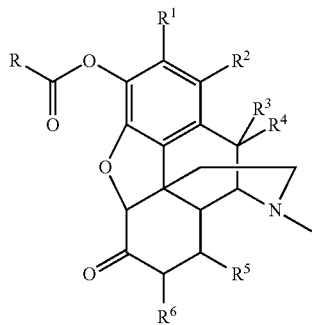

(I)

wherein:

R is selected from the group consisting of hydrocarbyl and substituted hydrocarbyl;

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$ are independently selected from the group consisting of hydrogen, hydrocarbyl, and substituted hydrocarbyl.

In preferred embodiments, $R^1$, $R^2$, $R^3$, $R^4$, $R^5$, and $R^5$ are hydrogen; and R is selected from the group consisting of alkyl, substituted alkyl, cycloalkyl, substituted cycloalkyl, carbocyclo, substituted carbocyclo, heterocyclo, substituted heterocyclo, aryl, and substituted aryl. In general, alkyl or cycloalkyl groups may be substituted in the carbon chain with a heteroatom or they may comprise a side chain substituent; and substituted carbocyclo, substituted heterocyclo, and substituted aryl groups may also comprise side chain substituents. Non-limiting examples of suitable heteroatoms include halogen, nitrogen, oxygen, phosphorous, silicon, and sulfur. Suitable side chain moieties include, without limit, alkyl, alkoxy, acyl, acyloxy, alkenyl, alkenoxy, aryl, aryloxy, amino, amino, acetal, carbamyl, carbocyclo, cyano, ester, ether, halogen, heterocyclo, hydroxy, keto, ketal, phospho, nitro, and thio.

In one exemplary embodiment, $R^1$, $R^2$, $R^3$, $R^4$, $R^5$, and $R^6$ are hydrogen; R is selected from the group consisting of n-butyl, isobutyl, cyclobutyl, n-pentyl, cyclopentyl, n-hexyl, cyclohexyl, n-heptyl, n-octyl, ethylhexyl, n-nonanyl, n-dodecanyl, n-tridecanyl, n-tetradecanyl, n-pentadecanyl, n-hexadecanyl, n-heptadecanyl, n-octadecanyl, n-iconsanyl, n-hemicosanyl, n-docosanyl, n-tricosanyl, n-tetracosanyl, n-heptacosanyl, benzyl, thienyl, thienylmethyl, furanyl, tetryhydrofuranyl, nicotinyl, methylthiomethyl, camphanyl, norbornanyl, methyglutaryl, methylsuccinyl, and methyladipoyl; and the optical activity of the compound is (−). In another exemplary embodiment, $R^1$, $R^2$, $R^3$, $R^4$, $R^5$, and $R^6$ are hydrogen; R is selected from the group consisting of methyl, ethyl, propyl, isopropyl, cyclopropyl, n-butyl, isobutyl, s-butyl, t-butyl, cyclobutyl, n-pentyl, cyclopentyl, n-hexyl, cyclohexyl, n-heptyl, n-octyl, ethylhexyl, n-nonanyl, n-dodecanyl, n-tridecanyl, n-tetradecanyl, n-pentadecanyl, n-hexadecanyl, n-heptadecanyl, n-octadecanyl, n-iconsanyl, n-hemicosanyl, n-docosanyl, n-tricosanyl, n-tetracosanyl, n-heptacosanyl, benzyl, phenyl, thienyl, thienylmethyl, furanyl, tetrahydrofuranyl, nicotinyl, methylthiomethyl, camphanyl, norbornanyl, methyglutaryl, methylsuccinyl, and methyladipoyl; and the optical activity of the compound is (+).

(b) 3-Substituted Carbonates of Hydromorphone

Another aspect of the present invention encompasses a compound comprising Formula (II) or a pharmaceutically acceptable salt thereof:

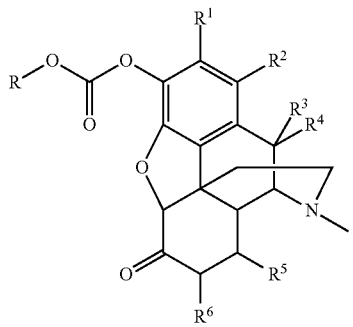

(II)

wherein:

R is selected from the group consisting of hydrocarbyl and substituted hydrocarbyl;

$R^1$ and $R^2$ are independently selected from the group consisting of hydrogen, halogen, {—}OH, {—}—$OR^7$, hydrocarbyl, and substituted hydrocarbyl; and $R^3$, $R^4$, $R^5$, $R^6$, and $R^7$, are independently selected from the group consisting of hydrogen, hydrocarbyl, and substituted hydrocarbyl.

In preferred embodiments, $R^1$, $R^2$, $R^3$, $R^4$, $R^5$, and $R^6$ are hydrogen; and R is selected from the group consisting of alkyl, substituted alkyl, cycloalkyl, substituted cycloalkyl, carbocyclo, substituted carbocyclo, heterocyclo, substituted heterocyclo, aryl, and substituted aryl. Substituted alkyl, cycloalkyl, carbocyclo, heterocyclo, and aryl are as defined above in section (I).

In an exemplary embodiment, $R^1$, $R^2$, $R^3$, $R^4$, $R^5$, and $R^6$ are hydrogen; R is selected from the group consisting of ethyl, n-propyl, isopropyl, cyclopropyl, n-butyl, isobutyl, s-butyl, f-butyl, cyclobutyl, n-pentyl, cyclopentyl, n-hexyl, ethylhexyl, cyclohexyl, cyclohexanemethylene, n-heptyl, n-octyl, n-nonanyl, n-dodecanyl, n-tetradecanyl, n-hexadecanyl, n-octadecanyl, n-docosanyl, n-tetracosanyl, n-octacosanyl, phenyl, benzyl, and menthyl; and the optical activity of the compound is (−). In another exemplary embodiment, $R^1$, $R^2$, $R^3$, $R^4$, $R^5$, and $R^6$ are hydrogen; R is selected from the group consisting of methyl, ethyl, n-propyl, isopropyl, cyclopropyl, n-butyl, isobutyl, s-butyl, t-butyl, cyclobutyl, n-pentyl, cyclopentyl, n-hexyl, ethylhexyl, cyclohexyl, cyclohexanemethylene, n-heptyl, n-octyl, n-nonanyl, n-dodecanyl, n-tetradecanyl, n-hexadecanyl, n-octadecanyl, n-docosanyl, n-tetracosanyl, n-octacosanyl, phenyl, benzyl, and menthyl; and the optical activity of the compound is (+).

(c) 3-Substituted Sulfonates of Hydromorphone

Still another aspect of the present invention provides a compound comprising Formula (II) or a pharmaceutically acceptable salt thereof:

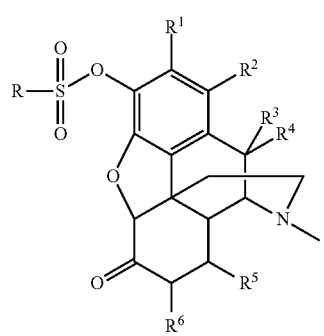

(III)

wherein:

R is selected from the group consisting of hydrocarbyl and substituted hydrocarbyl;

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$ are independently selected from the group consisting of hydrogen, hydrocarbyl, and substituted hydrocarbyl, In preferred embodiments, $R^1$, $R^2$, $R^3$, $R^4$, $R^5$, and $R^6$ are hydrogen. In other preferred embodiments, R is selected from the group consisting of alkyl, substituted alkyl, cycloalkyl, substituted cycloalkyl, carbocyclo, substituted carbocyclo, heterocyclo, substituted heterocyclo, aryl, and substituted aryl. Substituted alkyl, cycloalkyl, carbocyclo, heterocyclo, and aryl are as defined above in section (I).

In an exemplary embodiment, $R^1$, $R^2$, $R^3$, $R^4$, $R^5$, and $R^6$ are hydrogen; R is selected from the group consisting of ethyl, propyl, butyl, hexyl, and tolyl; and the optical activity of the compound is (−). In an exemplary embodiment, $R^1$, $R^2$, $R^3$, $R^4$, $R^5$, and $R^6$ are hydrogen; R is selected from the group consisting of methyl, ethyl, propyl, butyl, hexyl, phenyl, and tolyl; and the optical activity of the compound is (+).

(d) Pharmaceutically Acceptable Salts and Stereochemistry of the Compounds

Pharmaceutically acceptable salts of the compounds comprising Formulas (I), (II), or (III) include, without limitation, hydrochloride, hydrobromide, phosphate, sulfate, methanesulfonate, acetate, formate, tartrate, bitartrate, stearate, phthalate, hydroiodide, lactate, monohydrate, mucate, nitrate, phosphate, salicylate, phenylpriopionate, isobutyrate, hypophosphite, malate, maleate, citrate, isocitrate, succinate, lactate, gluconate, glucuronate, pyruvate, oxalate, fumarate, propionate, aspartate, glutamate, benzoate, terephthalate, and the like.

The optical activity, with respect to the rotation of polarized light, of the compounds comprising Formulas (I), (II), (III), or a pharmaceutically acceptable salt thereof may be (+) or (−); and the configuration of the chiral carbons C-5, C-13, C-14, and C-9, respectively, of the compounds comprising Formulas (I), (II), or (III) may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule.

(II) Pharmaceutical Compositions

Another aspect of the invention encompasses pharmaceutical compositions comprising at least one compound comprising Formulas (I), (II), (III), or a pharmaceutically acceptable salt thereof, and at least one pharmaceutically acceptable excipient. The amount of the compound(s) comprising Formulas (I), (II), or (III) in the pharmaceutical composition may range from about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, or about 99% by weight of the total pharmaceutical composition. Accordingly, the weight fraction of the excipient or combination of excipients in the pharmaceutical composition may be about 99%, about 97%, about 95% o, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 3%, or about 1% of the total weight of the pharmaceutical composition.

The pharmaceutical compositions detailed herein may be manufactured in one or several dosage forms. Suitable dosage forms also include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral (including subcutaneous, intradermal, intravenous, intramuscular, and intraperitoneal) administration; suspensions; emulsions; semisolids; or gels. Preferably the composition may be delivered via transdermal systems, patches, or liposome (or micelle) delivery systems.

Preparations for oral administration generally contain inert excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories. Transdermal administration may be via ointments, salves, gels, patches, or creams as generally known in the art. In preferred embodiments, the transdermal delivery system may be a matrix system, a reservoir system, or a system without rate-controlling membranes. In another preferred embodiment, the transdermal system may be a liposome delivery system or micelle delivery system.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. Other methods include, e.g., prilling, spray drying, pan coating, melt granulation, granulation, wurster coating, tangential coating, top spraying, extruding, coacervation and the like. For more details, see, e.g., Lachman et al., The Theory and Practice of Industrial Pharmacy (1986). Transdermal matrix, reservoir, membrane, liposome, and micelle delivery systems may be prepared using techniques well known to those of skill in the art.

In general, the pharmaceutical compositions of the invention may be used to treat pain and/or dry cough. The pharmaceutical compositions and, in particular, the transdermal delivery systems, may also be used for the management of oncologic and other chronic pain conditions.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocycle, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1

Identification of Candidate Prodrugs

The Log P (i.e., the n-octanol/water partition coefficient) and the calculated Log P (c Log P) values are useful indicators of the lipophilicity of a compound. Log P is an important physicochemical parameter for oral absorption because it relates to solubility and influences the ability of a compound to permeate through cell membranes. Previous studies have shown that compounds with Log P and c Log P values in the range of 2-3 have optimal transdermal/transmucosal transport in animals. Compounds having values of less than 2 are more hydrophilic and do not cross cell membranes effectively, and compounds having values greater than 3 tend to be too hydrophobic and are not taken up into the perfusion bed efficiently. Additionally, the molecular weight of the transported compound should not be greater than about 500 grams/mole, because large unassociated molecules have difficulty diffusing through the membranes.

ChemDraw Ultra 9.0 module of the ChemOffice Suite from Cambridge Scientific was used to calculate the molecular weight and partition coefficients for each candidate compound prior to synthesis. 3-O-alkyl, branched alkyl, cyclic alkyl esters and other select derivatives were modeled on Chem3D and HyperChem. Log P, c Log P, molecular volume and area, and estimated melting points were calculated after minimization using $MM^2$ and molecular dynamics to 600K. Results for selected compounds are set forth in Table 1.

TABLE 1

Calculated values for hydromorphone prodrug candidates.

| C—O Substituent | MW g/mole | LogP 3-O-ester/ carbonate | cLogP 3-O-ester/ carbonate |
|---|---|---|---|
| acetyl | 327.15 | 1.0 | 0.726 |
| propionyl | 341.16 | 1.65 | 1.085 |
| n-butanoyl | 355.18 | 2.07 | 1.614 |
| n-pentanoyl | 369.19 | 2.49 | 2.143 |
| n-hexanoyl | 383.27 | 2.91 | 2.672 |
| n-heptanoyl | 397.23 | 3.32 | 3.201 |
| n-octanoyl | 411.24 | 3.74 | 3.73 |
| cyclobutanoyl | 367.18 | 2.14 | 1.639 |
| ethylhexanoyl | 411.24 | 3.89 | 3.51 |
| isobutanoyl | 369.19 | 2.9 | 2.013 |
| (+)-menthyloxycarbonyl | 467.27 | 4.61 | 4.33 |
| methylthioacetyl | 373.47 | 1.38 | 0.805 |
| methoxyacetyl | 357.16 | 0.66 | 0.25 |

A series of 3-oxy-hydromorphone derivations were synthesized based on the Log P, c Log P, and MW values deemed optimal for transdermal/transmucosal transport. Compounds comprising Formula (I) (i.e., having an ester linkage) were prepared by reacting hydromorphone with approximately one mole of an appropriate R-acid chloride, anhydride, or mixed anhydride in a solvent, in the presence of an acid acceptor such as an alkali metal or alkaline earth metal carbonate or bicarbonate or a tertiary amine such as pyridine or triethylamine. A solution of the acylating agent in the reaction solvent was added to the reaction solvent containing the base and hydromorphone at a temperature generally ranging from 0° C. to room temperature. The reactants were kept in contact for 0.5 to 24 hours and the reaction was followed by HPLC analysis until substantially complete. Alternatively, compounds comprising Formula (I) were prepared by treating hydromorphone with an acid in the presence of a dehydrating agent, for example, dicyclohexylcarbodiimide. The reaction was generally run in the presence of a catalyst such as 4-dimethylaminopyridine in an aprotic solvent such as toluene, methylene chloride, chloroform, tetrahydrofuran or 1,2-dimethoxyethane. Compounds comprising Formula (II) (i.e., having a carbonate linkage) were prepared by reacting hydromorphone with a chloroformate having the formula RCOCl, wherein R is an alkoxy group, in the presence of an acid acceptor to afford the compound.

Examples 2-23 present the structures and analyses of the synthesized compounds.

Example 2

Synthesis of 3-(acetyloxy)-4,5α-epoxy-17-methyl-morphinan-6-one

Physical form: White solid
Sample: Gross Wt. 16.893 g; Tare 15.395 g; Net Wt. 1.498 g
Registry Number: 14696-22-1

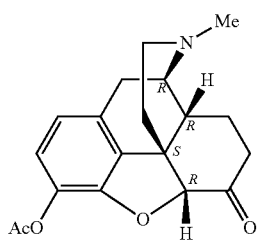

Chemical Formula: $C_{19}H_{21}NO_4$

Exact Mass: 327.15
Molecular Weight: 327.37
Mass Spec Analysis (m/z): 327.15 (100.0%), 328.15 (20.9%), 329.15 (2.9%)
Elemental Analysis: C, 69.71; H, 6.47; N, 4.28; O, 19.55

Example 3

Synthesis of 3-(ethylcarboxy)-4,5α-epoxy-17-methylmorphinan-6-one

Physical form: White solid
Sample: Gross Wt. 17.416 g; Tare 15.353 g; Net Wt, 2.063 g

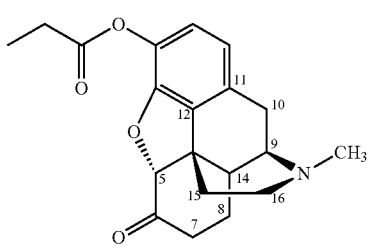

Chemical Formula: $C_{20}H_{23}NO_4$

Exact Mass: 341.16
Molecular Weight: 341.4
Mass Spec Analysis (m/z): 341.16 (100.0%), 342.17 (22.0%), 343.17 (3.1%)
Elemental Analysis: C, 70.36; H, 6.79; N, 4.10; O, 18.75

Example 4

Synthesis of 3-(isobutylcarboxy)-4,5α-epoxy-17-methylmorphinan-6-one

Physical form: White solid
Sample: Gross Wt. 17.323 g; Tare 15.278 g; Net Wt. 2.045 g

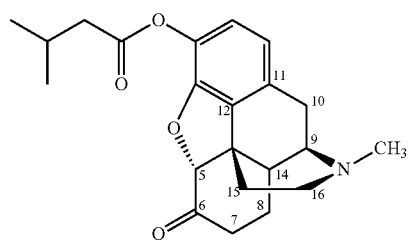

Chemical Formula: $C_{21}H_{25}NO_4$

Exact Mass: 355.18
Molecular Weight: 355.43
Mass Spec Analysis (m/z): 355.18 (100.0%), 356.18 (23.5%), 357.19 (2.6%)
Elemental Analysis: C, 70.96; H, 7.09; N, 3.94; O, 18.01

Example 5

Synthesis of 3-(cyclobutylcarboxy)-4,5α-epoxy-17-methylmorphinan-6-one

Physical form: White solid
Sample: Gross Wt. 16.580 g; Tare 15.321 g; Net Wt. 1.259 g

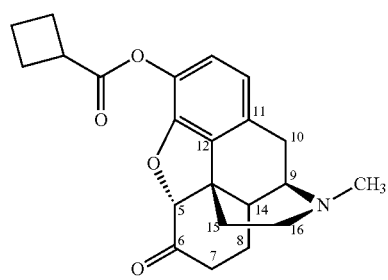

Chemical Formula: $C_{22}H_{25}NO_4$

Exact Mass: 367.18
Molecular Weight: 367.44
Mass Spec Analysis (m/z): 367.18 (100.0%), 368.18 (24.6%), 369.19 (2.8%)
Elemental Analysis: C, 71.91; H, 6.86; N, 3.81; O, 17.42

Example 6

Synthesis of 3-(n-butylcarboxy)-4,5α-epoxy-17-methylmorphinan-6-one

Physical form: Clear liquid
Sample: Gross Wt. 16.804 g; Tare 15.270 g; Net Wt. 1.534 g

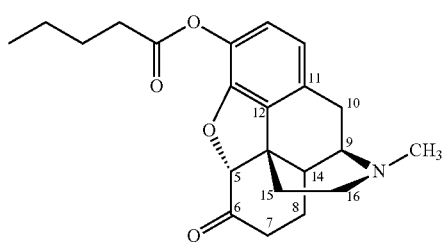

Chemical Formula: C₂₂H₂₇NO₄

Exact Mass: 369.19
Molecular Weight: 369.45
Mass Spec Analysis (m/z): 369.19 (100.0%), 370.20 (24.3%), 371.20 (3.6%)
Elemental Analysis: C, 71.52; H, 7.37; N, 3.79; O, 17.32

Example 7

Synthesis of 3-(n-pentylcarboxy)-4,5α-epoxy-17-methylmorphinan-6-one

Physical form: Clear liquid
Sample: Gross Wt. 16.982 g; Tare 15.425 g; Net Wt. 1.557 g

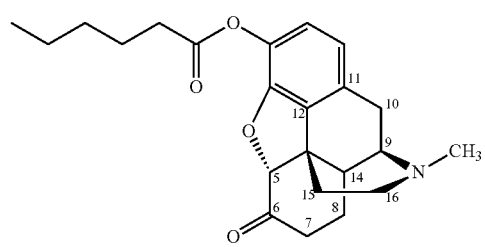

Chemical Formula: C₂₃H₂₉NO₄

Exact Mass: 383.21
Molecular Weight: 383.48
Mass Spec Analysis (m/z): 383.21 (100.0%), 384.21 (25.4%), 385.22 (3.1%)
Elemental Analysis: C, 72.04; H, 7.62; N, 3.65; O, 16.69

Example 8

Synthesis of 3-(n-hexylcarboxy)-4,5α-epoxy-17-methylmorphinan-6-one

Physical form: Clear liquid
Sample: Gross Wt. g; Tare g; Net Wt. g [Note—the values are missing]

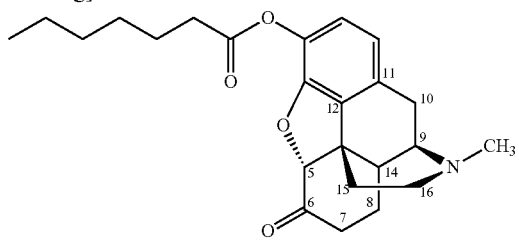

Chemical Formula: C₂₄H₃₁NO₄

Exact Mass: 397.23
Molecular Weight: 397.51
Mass Spec Analysis (m/z): 397.23 (100.0%), 398.23 (26.5%), 399.23 (4.3%)
Elemental Analysis: C, 72.52; H, 7.86; N, 3.52; O, 16.10

Example 9

Synthesis of 3-(n-heptylcarboxy)-4,5α-epoxy-17-methylmorphinan-6-one

Physical form: Clear liquid

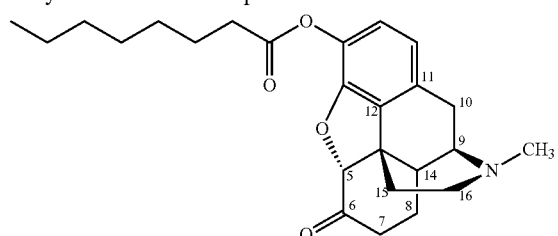

Chemical Formula: C₂₅H₃₃NO₄

Sample: Gross Wt. 17.169 g; Tare 15.465 g; Net Wt. 1.704 g
Exact Mass: 411.24
Molecular Weight: 411.53
Mass Spec Analysis (m/z): 411.24 (100.0%), 412.24 (27.4%), 413.25 (4.5%)
Elemental Analysis: C, 72.96; H, 8.08; N, 3.40; O, 15.55

Example 10

Synthesis of 3-(3'-heptylcarboxy)-4,5α-epoxy-17-methylmorphinan-6-one

Physical form: Clear liquid
Sample: Gross Wt. 17.082 g; Tare 15.251 g; Net Wt. 1.831 g

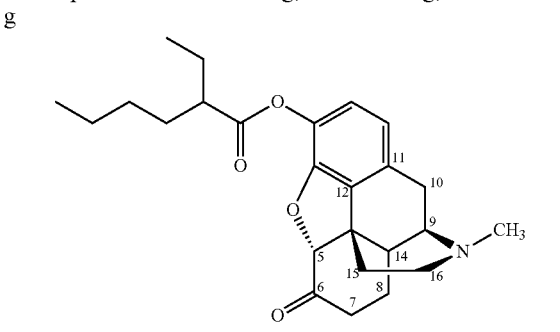

Chemical Formula: C₂₅H₃₃NO₄

Exact Mass: 411.24
Molecular Weight: 411.53
Mass Spec Analysis (m/z): 411.24 (100.0%), 412.24 (27.4%), 413.25 (4.5%)
Elemental Analysis: C, 72.96; H, 8.08; N, 3.40; O, 15.55

Example 11

Synthesis of 3{(1'S)-(+)-menthyloxycarboxyl}-4,5α-epoxy-17-methylmorphinan-6-one Physical form: white solid
Sample: Gross Wt. 17.998 g; Tare 15.337 g; Net Wt. 2.661 g

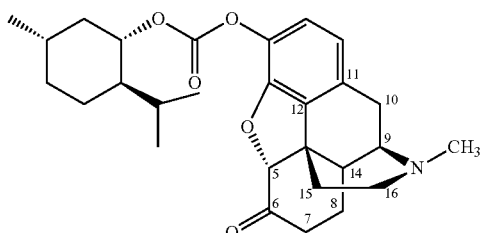

Chemical Formula: C₂₈H₃₇NO₅

Exact Mass: 467.27

Molecular Weight: 467.6

Mass Spec Analysis (m/z): 467.27 (100.0%), 468.27 (30.9%), 469.27 (5.6%)

Elemental Analysis: C, 71.92; H, 7.98; N, 3.00; O, 17.11

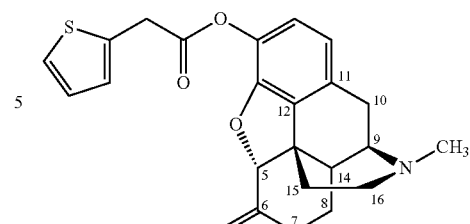

Chemical Formula: C₂₃H₂₃NO₄S

Exact Mass: 409.13

Molecular Weight: 409.5

Mass Spec Analysis (m/z): 409.13 (100.0%), 410.14 (25.3%), 411.13 (4.5%), 411.14 (4.2%), 410.13 (1.2%), 412.13 (1.1%)

Elemental Analysis: C, 67.46; H, 5.66; N, 3.42; O, 15.63, S, 7.83

Example 12

Synthesis of 3-(2'-thienylcarboxy)-4,5α-epoxy-17-methylmorphinan-6-one

Physical form: Off-white solid

Sample: Gross Wt. 17.352 g; Tare 15.401 g; Net Wt. 1.951 g

Example 14

Synthesis of 3-(3'-thienylacetyloxy)-4,5α-epoxy-17-methylmorphinan-6-one

Physical form: Off-white solid

Sample: Gross Wt, 16.786 g; Tare 15.390 g; Net Wt. 1.396 g

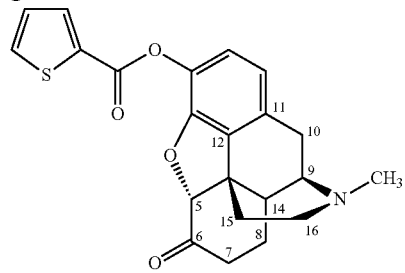

Chemical Formula: C₂₂H₂₁NO₄S

Exact Mass: 395.12

Molecular Weight: 395.47

Mass Spec Analysis (m/z): 395.12 (100.0%), 396.12 (25.1%), 397.11 (4.5%), 397.13 (2.8%), 398.12 (1.1%), 397.12 (1.1%)

Elemental Analysis: C, 66.82; H, 5.35; N, 3.54; O, 16.18, S, 18.11

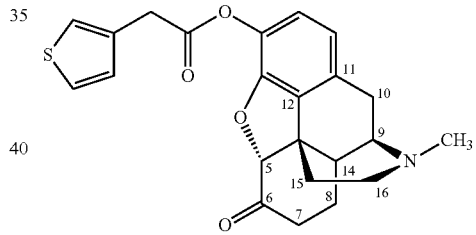

Chemical Formula: C₂₃H₂₃NO₄S

Exact Mass: 409.13

Molecular Weight: 409.5

Mass Spec Analysis (m/z): 409.13 (100.0%), 410.14 (25.3%), 411.13 (4.5%), 411.14 (4.2%), 410.13 (1.2%), 412.13 (1.1%)

Elemental Analysis: C, 67.46; H, 5.66; N, 3.42; O, 15.63, S, 7.83

Example 13

Synthesis of 3-(2'-thienylacetyloxy)-4,5α-epoxy-17-methylmorphinan-6-one

Physical form: Off-white solid

Sample: Gross Wt. 16.947 g; Tare 15.278 g; Net Wt. 1.669 g

Example 15

Synthesis of 3-(2'-tetrahydrofuranyloxy)-4,5α-epoxy-17-methylmorphinan-6-one

Physical form; amorphous solid

Sample: Gross Wt. 17.336 g; Tare 15.440 g; Net Wt. 1.896 g

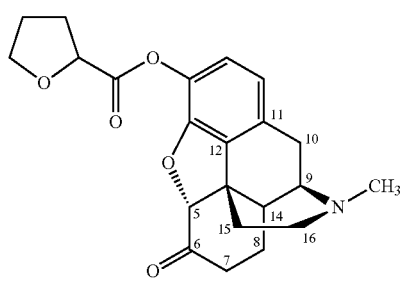

Chemical Formula: $C_{22}H_{25}NO_5$

Exact Mass: 383.17
Molecular Weight: 383.44
Mass Spec Analysis (m/z): 383.17 (100.0%), 384.18 (24.3%), 385.18 (3.8%)
Elemental Analysis: C, 68.91; H, 6.57; N, 3.65; O, 20.86

Example 16

Synthesis of 3-(3'-tetrahydrofuranyloxy)-4,5α-epoxy-17-methylmorphinan-6-one

Physical form: amorphous solid
Sample: Gross Wt. 17.150 g; Tare 15.433 g; Net Wt. 1.717 g

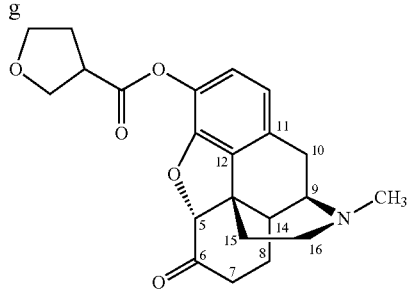

Chemical Formula: $C_{22}H_{25}NO_5$

Exact Mass: 383.17
Molecular Weight: 383.44
Mass Spec Analysis (m/z): 383.17 (100.0%), 384.18 (24.3%), 385.18 (3.8%)
Elemental Analysis: C, 68.91; H, 6.57; N, 3.65; O, 20.86

Example 17

Synthesis of 3-(isobutoxycarboxy)-4,5α-epoxy-17-methylmorphinan-6-one

Physical form: white solid

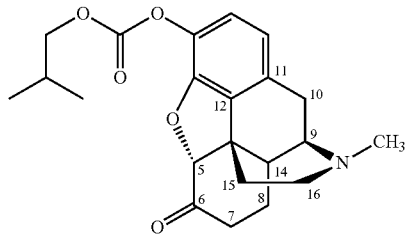

Chemical Formula: $C_{22}H_{27}NO_5$

Sample: Gross Wt. 17.050 g; Tare 15.355 g; Net Wt. 1.695 g

Exact Mass: 385.19
Molecular Weight: 385.45
Mass Spec Analysis (m/z): 385.19 (100.0%), 386.19 (24.4%), 387.20 (2.8%), 387.19 (1.1%)
Elemental Analysis: C, 68.55; H, 7.06; N, 3.63; O, 20.75

Example 18

Synthesis of 3-(nicotinylcarboxy)-4,5α-epoxy-17-methylmorphinan-6-one

Physical form: Off-white solid
Sample: Gross Wt. 16.815 g; Tare 15.501 g; Net Wt. 1.314 g

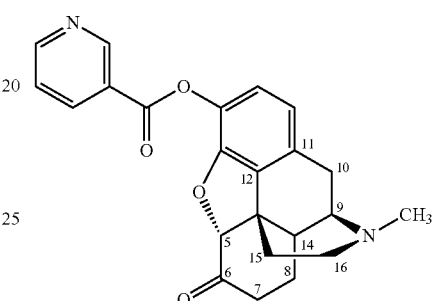

Chemical Formula: $C_{23}H_{22}N_2O_4$

Exact Mass: 390.16
Molecular Weight: 390.43
Mass Spec Analysis (m/z): 390.16 (100.0%), 391.16 (25.3%), 392.16 (4.0%)
Elemental Analysis: C, 70.75; H, 5.68; N, 7.17; O, 16.39

Example 19

Synthesis of 3-(benzenesulfonyloxy)-4,5α-epoxy-17-methylmorphinan-6-one

Physical form: white solid

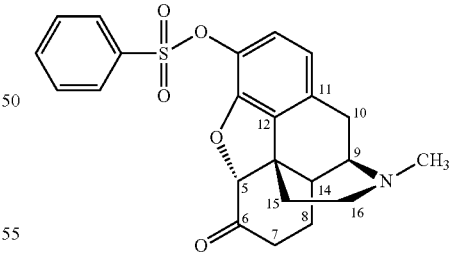

Chemical Formula: $C_{23}H_{23}NO_5S$

Sample: Gross Wt. 17.141 g; Tare 15.311 g; Net Wt. 1.830 g

Exact Mass: 425.13
Molecular Weight: 425.5
Mass Spec Analysis (m/z): 425.13 (100.0%), 426.13 (26.2%), 427.13 (5.8%), 427.14 (3.1%), 428.13 (1.2%)
Elemental Analysis: C, 64.92; H, 5.45; N, 3.29; O, 18.80, S, 7.54

Example 20

Synthesis of 3-(α-methylthioacetyl)-4,5α-epoxy-17-methylmorphinan-6-one

Physical form: amorphous solid
Sample: Gross Wt. 17.276 g; Tare 15.314 g; Net Wt. 1.962 g

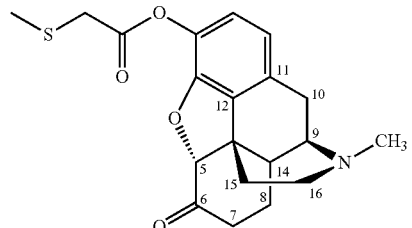

Chemical Formula: $C_{20}H_{23}NO_4S$

Exact Mass: 373.13
Molecular Weight: 373.47
Mass Spec Analysis (m/z): 373.13 (100.0%), 374.14 (22.0%), 375.13 (4.5%), 375.14 (3.4%), 374.13 (1.2%), 376.13 (1.0%)
Elemental Analysis: C, 64.32; H, 6.21; N, 3.75; O, 17.14, S, 8.59

Example 21

Synthesis of 3-{(1S)-(−)-camphanyl}-4,5α-epoxy-17-methylmorphinan-6-one

Physical form: amorphous solid

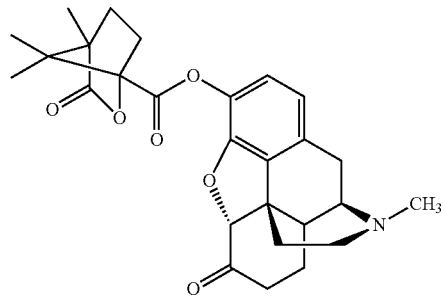

Chemical Formula: $C_{27}H_{31}NO_6$

Sample: Gross Wt. 16.113 g; Tare 15.283 g; Net Wt. 0.830 g (~85%, balance hydromorphone)
Exact Mass: 465.22
Molecular Weight: 465.54
Mass Spec Analysis (m/z): 465.22 (100.0%), 466.22 (29.8%), 467.22 (5.6%)
Elemental Analysis: C, 69.66; H, 6.71; N, 3.01; O, 20.62

Example 22

Synthesis of 3-(cyclopentylcarboxy)-4,5α-epoxy-17-methylmorphinan-6-one

Physical form: White solid
Sample: Gross Wt. 15.254 g; Tare 16.563 g; Net Wt. 1.309 g

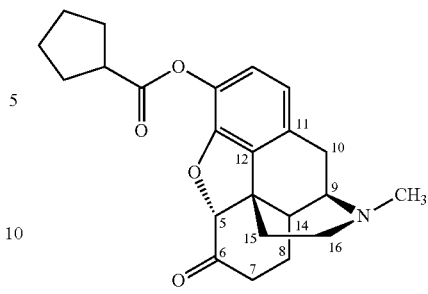

Chemical Formula: $C_{23}H_{27}NO_4$

Exact Mass: 381.19
Molecular Weight: 381.46
Mass Spec Analysis (m/z): 381.19 (100.0%), 382.20 (25.3%), 383.20 (3.9%)
Elemental Analysis: C, 72.42; H, 7.13; N, 3.67; O, 16.78

Example 23

Synthesis of (2'-furanylcarboxy)-4,5α-epoxy-17-methylmorphinan-6-one

Physical form: Off-white solid
Sample: Gross Wt. 15.473 g; Tare 17.284 g; Net Wt. 1.811 g

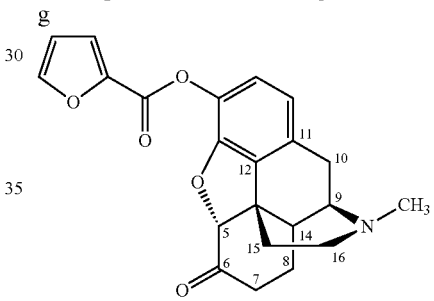

Chemical Formula: $C_{22}H_{21}NO_5$

Exact Mass: 379.14
Molecular Weight: 379.41
Mass Spec Analysis (m/z): 379.14 (100.0%), 380.15 (24.2%), 381.15 (3.8%)
Elemental Analysis: C, 69.64; H, 5.58; N, 3.69; O, 21.08

What is claimed is:
1. A compound of Formula (I) or a pharmaceutically acceptable salt thereof:

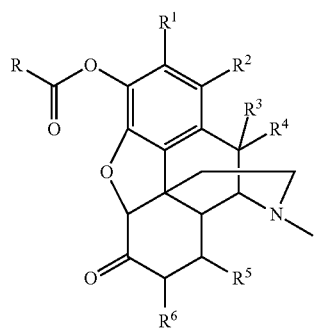

(I)

wherein:

R is selected from the group consisting of
(i) n-butyl, isobutyl, cyclobutyl, n-pentyl, cyclopentyl, n-hexyl, cyclohexyl, n-heptyl, n-octyl, ethylhexyl, n-nonanyl, n-dodecanyl, n-tridecanyl, n-tetradecanyl, n-pentadecanyl, n-hexadecanyl, n-heptadecanyl, n-octadecanyl, n-iconsanyl, n-hemicosanyl, n-docosanyl, n-tricosanyl, n-tetracosanyl, n-heptacosanyl, benzyl, thienyl, thienylmethyl, furanyl, tetryhydrofuranyl, methylthiomethyl, camphanyl, norbornanyl, methyglutaryl, methylsuccinyl, and methyladipoyl, wherein the optical activity of the compound is (−), or
(ii) ethyl, propyl, isopropyl, cyclopropyl, n-butyl, isobutyl, s-butyl, t-butyl, cyclobutyl, n-pentyl, cyclopentyl, n-hexyl, cyclohexyl, n-heptyl, n-octyl, ethylhexyl, n-nonanyl, n-dodecanyl, n-tridecanyl, n-tetradecanyl, n-pentadecanyl, n-hexadecanyl, n-heptadecanyl, n-octadecanyl, n-iconsanyl, n-hemicosanyl, n-docosanyl, n-tricosanyl, n-tetracosanyl, n-heptacosanyl, benzyl, phenyl, thienyl, thienylmethyl, furanyl, tetryhydrofuranyl, methylthiomethyl, camphanyl, norbornanyl, methyglutaryl, methylsuccinyl, and methyladipoyl, wherein the optical activity of the compound is (+);

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$, are independently selected from the group consisting of hydrogen, hydrocarbyl, and substituted hydrocarbyl.

2. The compound of claim 1, wherein $R^1$, $R^2$, $R^3$, $R^4$, $R^5$, and $R^6$ are hydrogen.

3. The compound of claim 1, wherein R is selected from the group consisting of n-butyl, isobutyl, cyclobutyl, n-pentyl, cyclopentyl, n-hexyl, cyclohexyl, n-heptyl, n-octyl, ethylhexyl, n-nonanyl, n-dodecanyl, n-tridecanyl, n-tetradecanyl, n-pentadecanyl, n-hexadecanyl, n-heptadecanyl, n-octadecanyl, n-iconsanyl, n-hemicosanyl, n-docosanyl, n-tricosanyl, n-tetracosanyl, n-heptacosanyl, benzyl, thienyl, thienylmethyl, furanyl, tetryhydrofuranyl, methylthiomethyl, camphanyl, norbornanyl, methyglutaryl, methylsuccinyl, and methyladipoyl; and the optical activity of the compound is (−).

4. The compound of claim 1, wherein R is selected from the group consisting of ethyl, propyl, isopropyl, cyclopropyl, n-butyl, isobutyl, s-butyl, t-butyl, cyclobutyl, n-pentyl, cyclopentyl, n-hexyl, cyclohexyl, n-heptyl, n-octyl, ethylhexyl, n-nonanyl, n-dodecanyl, n-tridecanyl, n-tetradecanyl, n-pentadecanyl, n-hexadecanyl, n-heptadecanyl, n-octadecanyl, n-icosanyl, n-emicosanyl, n-docosanyl, n-tricosanyl, n-tetracosanyl, n-heptacosanyl, benzyl, phenyl, thienyl, thienylmethyl, furanyl, tetryhydrofuranyl, methylthiomethyl, camphanyl, norbornanyl, methyglutaryl, methylsuccinyl, and methyladipoyl; and the optical activity of the compound is (+).

5. The compound of claim 1, wherein the configuration of C-5, C-13, C-14, and C-9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

6. A compound of Formula (II) or a pharmaceutically acceptable salt thereof:

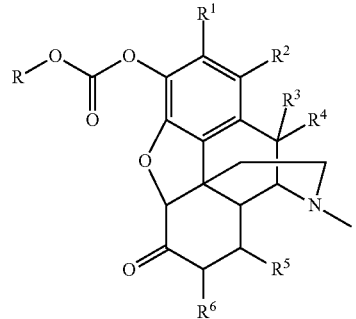

(II)

wherein:

R is selected from the group consisting of
(i) ethyl, n-propyl, isopropyl, cyclopropyl, n-butyl, isobutyl, s-butyl, t-butyl, cyclobutyl, n-pentyl, cyclopentyl, n-hexyl, ethylhexyl, cyclohexyl, cyclohexanemethylene, n-heptyl, n-octyl, n-nonanyl, n-dodecanyl, n-tetradecanyl, n-hexadecanyl, n-octadecanyl, n-docosanyl, n-tetracosanyl, n-octacosanyl, phenyl, and menthyl, wherein the optical activity of the compound is (−), or
(ii) methyl, ethyl, n-propyl, isopropyl, cyclopropyl, n-butyl, isobutyl, s-butyl, t-butyl, cyclobutyl, n-pentyl, cyclopentyl, n-hexyl, ethylhexyl, cyclohexyl, cyclohexanemethylene, n-heptyl, n-octyl, n-nonanyl, n-dodecanyl, n-tetradecanyl, n-hexadecanyl, n-octadecanyl, n-docosanyl, n-tetracosanyl, n-octacosanyl, phenyl, and menthyl, wherein the optical activity of the compound is (+);

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$, are independently selected from the group consisting of hydrogen, hydrocarbyl, and substituted hydrocarbyl.

7. The compound of claim 6, wherein $R^1$, $R^2$, $R^3$, $R^4$, $R^5$, and $R^6$ are hydrogen.

8. The compound of claim 6, wherein R is selected from the group consisting of ethyl, n-propyl, isopropyl, cyclopropyl, n-butyl, isobutyl, s-butyl, t-butyl, cyclobutyl, n-pentyl, cyclopentyl, n-hexyl, ethylhexyl, cyclohexyl, cyclohexanemethylene, n-heptyl, n-octyl, n-nonanyl, n-dodecanyl, n-tetradecanyl, n-hexadecanyl, n-octadecanyl, n-docosanyl, n-tetracosanyl, n-octacosanyl, phenyl, and menthyl; and the optical activity of the compound is (−).

9. The compound of claim 6, wherein R is selected from the group consisting of methyl, ethyl, n-propyl, isopropyl, cyclopropyl, n-butyl, isobutyl, s-butyl, t-butyl, cyclobutyl, n-pentyl, cyclopentyl, n-hexyl, ethylhexyl, cyclohexyl, cyclohexanemethylene, n-heptyl, n-octyl, n-nonanyl, n-dodecanyl, n-tetradecanyl, n-hexadecanyl, n-octadecanyl, n-docosanyl, n-tetracosanyl, n-octacosanyl, phenyl, and menthyl; and the optical activity of the compound is (+).

10. The compound of claim 6, wherein the configuration of C-5, C-13, C-14, and C-9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule.

11. A compound of Formula (III) or a pharmaceutically acceptable salt thereof:

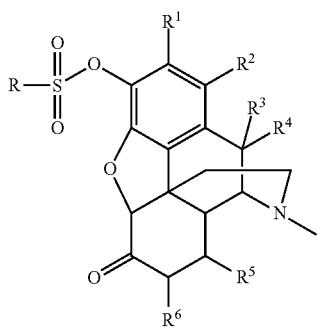

(III)

wherein:

R is selected from the group consisting of (i) ethyl, propyl, butyl, hexyl, and tolyl, wherein the optical activity of the compound is (−), or (ii) methyl, ethyl, propyl, butyl, hexyl, phenyl, and tolyl, wherein the optical activity of the compound is (+);

$R^1$ and $R^2$ are independently selected from the group consisting of hydrogen, halogen, {—}OH, {—}$OR^7$, hydrocarbyl, and substituted hydrocarbyl; and $R^3$, $R^4$, $R^5$, $R^6$, and $R^7$, are independently selected from the group consisting of hydrogen, hydrocarbyl, and substituted hydrocarbyl.

12. The compound of claim 11, wherein $R^1$, $R^2$, $R^3$, $R^4$, $R^5$, and $R^6$ are hydrogen.

13. The compound of claim 11, wherein R is selected from the group consisting of ethyl, propyl, butyl, hexyl, and tolyl; and the optical activity of the compound is (−).

14. The compound of claim 11, wherein R is selected from the group consisting of methyl, ethyl, propyl, butyl, hexyl, phenyl, and tolyl; and the optical activity of the compound is (+).

15. The compound of claim 11, wherein the configuration of C5, C13, C14, and C9, respectively, is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided that the C15 and the C16 carbons are both either on the alpha face of the molecule or the beta face of the molecule.

* * * * *